United States Patent [19]

Karny et al.

[11] Patent Number: 4,569,590

[45] Date of Patent: Feb. 11, 1986

[54] METHOD AND APPARATUS FOR MEASURING THE INDEX OF REFRACTION OF FLUIDS

[75] Inventors: Ziv Karny, Omer; Oded Kafri, Beer-Sheva; Eliezer Keren, Arad, all of Israel

[73] Assignee: The State of Israel, Atomic Energy Commission, Beer-Sheva, Israel

[21] Appl. No.: 463,614

[22] Filed: Feb. 3, 1983

[30] Foreign Application Priority Data

Jun. 24, 1982 [IL] Israel .................................. 66127

[51] Int. Cl.⁴ .......................................... G01N 21/41
[52] U.S. Cl. .................................................. 356/128
[58] Field of Search ...................... 356/374, 376, 128; 250/237

[56] References Cited

U.S. PATENT DOCUMENTS 3,612,696 10/1971 Broerman ........................... 356/128

OTHER PUBLICATIONS

Oster et al., Moire Patterns, Scientific American, May, 1963, pp. 54–64.
Yoshino et al., Doubling and Visibility Enhancement of Moire Fringes of the Summation Type, Applied Optics, pp. 1124–1126, vol. 15, No. 5, May, '76.
Moser et al., A Method for Measurement of the Refracting Index of Liquids and Solids by the Moire Pattern Technique, Bull. Soc. Physicians Republ. Socialiste Macedoine, (Yugoslavia) vol. 27, 1977, pp. 55–65.

*Primary Examiner*—F. L. Evans
*Attorney, Agent, or Firm*—Browdy and Neimark

[57] ABSTRACT

A system for determining the index of refraction of a sample fluid in which light from a collimated light source is directed through a light pervious cell in which sample and reference fluids are held. The light from the collimated light source which is transmitted through the cell is deflected and is then directed through a pair of gratings to establish patterns. When the cell contains a reference fluid therein, first patterns are established, and second patterns are then established by replacing the reference fluid with the sample fluid. A measurement of the change between the first patterns and the second patterns is used for determining the index of refraction of the sample fluid.

9 Claims, 4 Drawing Figures

METHOD AND APPARATUS FOR MEASURING THE INDEX OF REFRACTION OF FLUIDS

This invention is concerned with systems and methods for measuring the index of refraction of fluids and more particularly is directed to systems and methods for making such measurements using Moire deflectometry.

The index of refractive of a fluid provides information such as the temperature, pressure, chemical composition of transparent materials and particularly transparent fluids including liquids, gases and vapors. Index of refraction measurements are used, for example, in the food processing industry to ascertain the composition of certain sucrose mixtures.

Different techniques are used to measure the index of refraction of solids, liquids and gases. For example, the index of refraction of gases is usually measured by interferometric methods while that of liquids is usually measured by Abbe refractometry which is based on total reflection.

The prior art methods and systems of measuring the index of refraction of fluids utilize interferometry to measure the differences in the optical lengths of light rays going through the material whose indexes of refraction are being determined. The optical lengths are proportional to the refractive index. The accuracy of the prior art methods is diffraction limited. The measurements of the index of refraction of gases is done using interferometry. Interferometry requires extreme mechanical stability. Thus, for example, a system whose mechanical stability is less than 1/10 the wavelength of the light being used is subject to crucial errors. In addition rigidly controlled laboratory conditions are required for the use of the equipment to assure the mechanical stability and the accuracy of the measurements. Thus, highly skilled personnel are required to operate the systems. Therefore the presently known systems used to measure the index of refraction of materials are either limited in scope of extremely costly.

Accordingly it is an object of the present invention to provide new and improved systems for determining the index of refraction of fluids in which the above-referred to disadvantages are substantially reduced or overcome.

According to the present invention a system is provided for determining the index of refraction of a sample fluid, said system comprising:
collimated light source means,
light pervious cell means for holding fluids and deflecting light passing therethrough,
Moire pattern establishing means for establishing Moire patterns using light from said collimated light source means transmitted through said cell means,
means for superimposing first Moire patterns established using said Moire pattern establishing means when said cell means has a reference fluid therein with a known index of refraction and second Moire pattern rotated from said first Moire pattern and established using said Moire pattern establishing means with said sample fluid in said cell means to thereby establish a third Moire pattern, and
means for measuring characteristics of said Moire patterns to use in computing the index of refraction of said sample fluid.

Among the features of the system are included means for computing the index of refraction of said sample fluid as a function of the pitches p and p' of said second and third Moire patterns respectively. The index of refraction can be obtained by this method when the fluid is a gas, a liquid or a vapor.

The method for determining the index of refraction of the sample fluid comprises the steps of:
Preparing a Moire pattern by transmitting collimated light rays through a fluid with a known index of refraction,
deflecting that pattern by transmitting the collimated light rays through a fluid with an unknown index of refraction,
measuring the deflection caused by the change of fluid, and
computing the index of refraction as a function of the deflection caused by the change of fluids.

In the system, the cell is unique, among other ways, in that it is compartmentalized. The compartments are separated by means such as lens means which in conjunction with the fluids in the cell deflects collimated light rays. A preferred embodiment of the cell comprises an inner compartment and an outer compartment separated by the lens means.

A feature of the system or method is that it can be readily automated to provide "go"-"no go" results or automatic index of refraction readouts at a relatively low cost and with relatively unskilled personnel.

Accordingly a further feature of the invention includes an unsophisticated system wherein said Moire patterns are projected onto a screen and a camera is used for obtaining a double exposure of said first and second Moire patterns to obtain said third Moire pattern and wherein the pitch characteristics of said third Moire pattern can be physically measured to obtain the index of refraction of the sample fluid in the cell.

It should be recognised that the cell of the preferred embodiment can be used in interferometer measurements also, particularly in shearing interferometry. Further the equipment and methods disclosed herein provide tests at "real" times.

The operation and utilization of the present invention will be more fully apparent from the description of a preferred embodiment taken in conjunction with the following drawings, in which.

Figure 1:
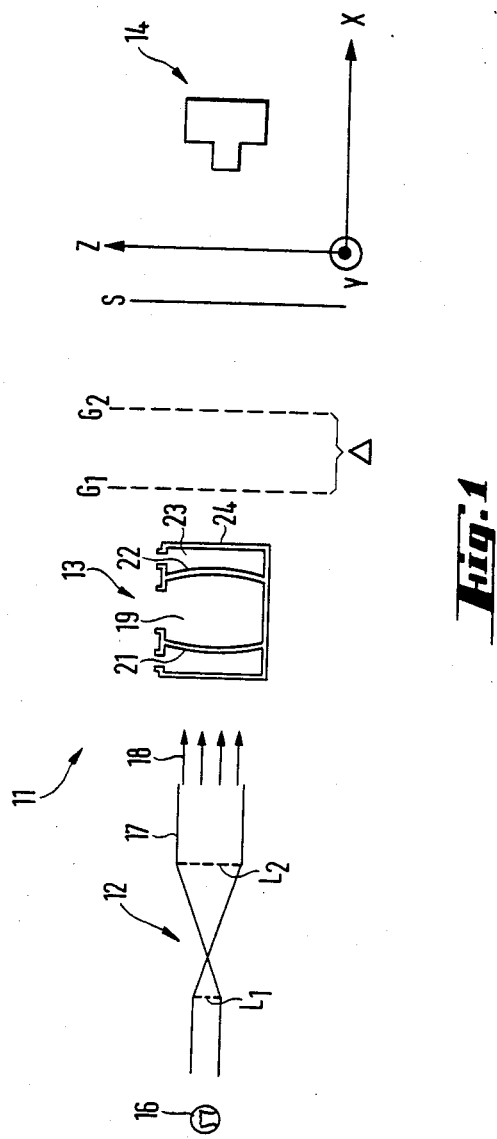
FIG. 1 is a simplified block diagram showing of an exemplary system for determining the index of refraction of fluids.

A system 11 for measuring the index of refraction by Moire deflectometry is shown in FIG. 1. The system comprises a source of collimated light shown generally as 12, a cell for holding the fluid whose index of refraction is being measured indicated as 13, a pair of gratings $G_1$ and $G_2$ spaced apart by a known distance $\Delta$ and a Moire pattern receiver such as screen S 28 on which the Moire pattern is projected.

Means are provided for recording what is on the screen of FIG. 1a. This means is indicated by the camera 14. Axes extending in the X, Y and Z direction are shown for purposes of orientation and explanation of the operation of the system. The X, Y and Z axes, of course, are imaginary.

The collimated light source 12 comprises an electric light source 16 whose rays are collimated by a telescope 17 having lenses $L_1$ and $L_2$. The collimated light beams 18 are emitted from the telescope and directed to the cell 13. The cell 13 is transparent so that the light passes through it.

Means are provided for moving the light passing through the cell. More particularly the inner portion of the cell 19 is defined by a pair of lenses 21 and 22 having an infinite focal length.

It should be understood while lenses 21 and 22 are shown, other means for bending light rays fixed amounts such as even tilted windows forming an empty wedge can be used within the scope of the invention. The purpose of the cell is to provide a comparison of the deflection of the collimated light obtained using a fluid of known index of refraction and a fluid of unknown index of refraction.

Figure 2:
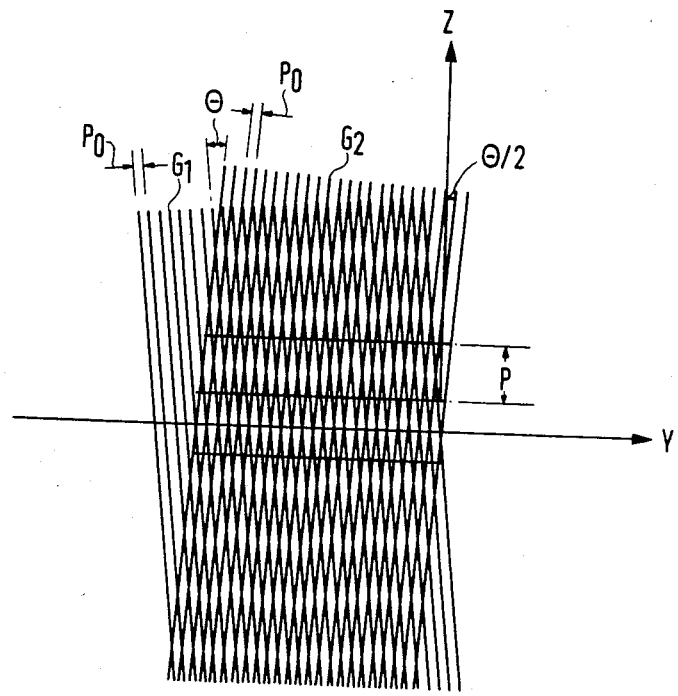
FIG. 2 is a showing of gratings $G_1$ and $G_2$ used in establishing the Moire patterns.

The outer compartment of the cell indicated at 23 has windows such as windows 24 which may extend around the cell. The entrance to the inner compartment 19 and also to the outer compartment 23 can be readily sealed in any well known manner to enable the cell to be filled with gases, vapor or mixtures of liquids and gases or vapors. The gratings $G_1$ and $G_2$ are rotated relative to each other so that the angle between the lines of the gratings is $\theta$ and in the preferred embodiment the pitch of the lines of gratings $G_1$ and $G_2$ are each equal to $p_o$ as shown in FIG. 2. The lines of the gratings extend in the YZ plane as shown in FIG. 2.

Returning to FIG. 1, the cell 13 is first filled with a solution of a known index of refraction preferably water for example, at a precise temperature. The collimated light beam is transmitted through the cell 13, the gratings $G_1$ and $G_2$ spaced apart by a distance $\Delta$ and projected onto the screen to provide a Moire pattern on the screen having a pitch p. The inner compartment 19 of the cell 13 is then filled with a sample fluid of unknown index of refraction. If the sample fluid has a different index of refraction than water, the Moire pattern on the screen will be rotated. The rotation occurs because the focal length of the cell is changed because of the change in the index of refraction of the fluid in the cell. Therefore the change in focal length is a function of the index of refraction of the unknown fluid.

In the preferred embodiment each of the lenses have two identical radii of curvature, that is they are both zero diopter lenses. The use of zero diopter lenses increases the dynamic range of the measurement. It is not absolutely necessary to the method or the system but is preferred. It should be noted that if the index of refraction of the fluid in the outer compartment and the inner compartment are equal, then the collimated beam passing through the cell is not distorted or rotated. However, if the index of refraction of the sample fluid is greater than the index of refraction of the reference fluid, a positive lens is produced, while if the index of refraction of the sample fluid is less than the index of refraction of the reference fluid a negative lens is produced.

Since the amount of rotation of the Moire pattern in the system is a direct function of the index of refraction of the fluid in the inner compartment the index of refraction of the sample fluid can be determined merely by measuring the variation in the pitch of the grating of the Moire pattern finally produced. It should be noted that the amount of deflection or rotation can also be measured by measuring the actual distortion of a line in the Moire pattern on the YZ projection on the screen. However by utilizing a camera to take a picture of the projections on the screen and obtaining a double exposure another (3rd) Moire pattern is produced. By using the pitches $p_o$ of the original gratings, the pitch p of the original Moire pattern when the lens is comprised of a fluid of known index of refraction, and the pitch p' of the Moire pattern obtained with the double exposure after the sample fluid is placed in the inner compartment of the cell, the index of refraction of the sample fluid can be calculated.

The fact that the rotation of the pattern provides the desired index of refraction can be shown mathematically. For example, the general equation of a lens is given by:

$$1/f = (n_s - n_g)1/r_1 + (n_g - n_r)1/n_2$$

where $n_g$ is the index of refraction of the glass, f is the focal length of the lens, $n_s$ is the index of refraction of the sample fluid, $n_r$ is the index of refraction of the reference or known fluid, $r_1$ is the radius of curvature of the sample side and $r_2$ is the radius of curvature of the reference side of the lens in the cell.

The index of refraction of the glass and of the reference fluid remains fixed during the measurement. Therefore the equation of the lens can be reduced to $1/f = n_s/r_1 + C$ *where C is a constant. Changing the focal lens rotates the Moire patterns.*

Figure 3:
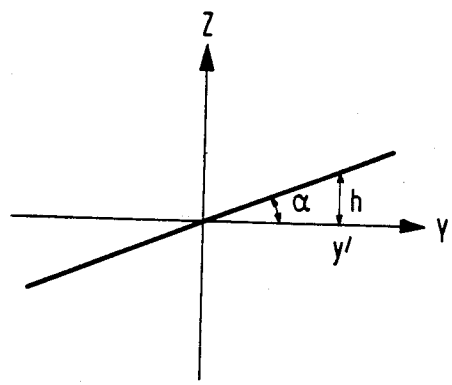
FIG. 3 is a graphical showing of an angle $\alpha$ used in determining the index of refraction.

FIG. 3 illustrates the rotation. An ideal lens deflects the perpendicular ray so that at a given point y' on the Y axis the ray will reach the focal point on the X axis. For a focal length f the deflection angle in the XY plane at a point y' is $\phi = \arctan(y'/f)$. In the Moire patterns on the screen (called the deflectogram) one observes a shift of the Moire pattern by an amount h given by the following equation:

$$h = (\phi \Delta)/\theta$$

where $\Delta$ is the difference between gratings, or $$h = \frac{\Delta \arctan(Y'/f)}{\theta}$$

For small angle approximation it can be assumed that the $\arctan(y'/f) = y'/f$. This equation gives good results of up to 2.5% for $\phi$ less than 15°. Therefore $h/y' = \tan \alpha$ or $\Delta/f\theta$. As shown in FIG. 3 the new lines of the Moire pattern are straight and are rotated by an angle $\alpha$. From the previous equations it can be stated that:

$$\frac{n_s}{r_1} + C = \frac{\theta \tan \alpha}{\Delta}.$$

To remove the constant C the last equation is differentiated to give a new equation;

$$\frac{d(\tan \alpha)}{dn_s} = \frac{\Delta}{\theta \, r_1}.$$

Note that the measurement of $\alpha$ and the calculation of the difference between the index of refraction of the sample fluid and the index of refraction of the reference fluid can be done in various ways using different kinds of known light detectors.

Figure 4:
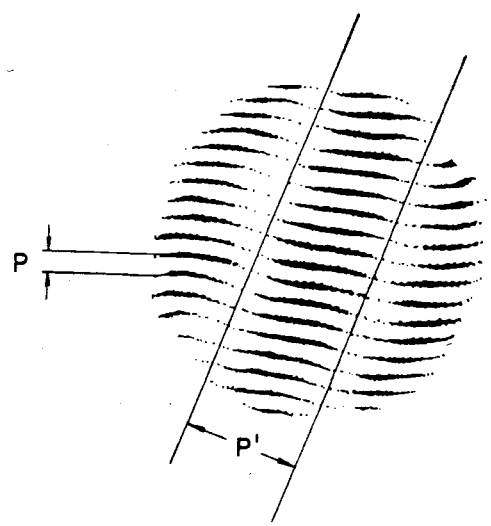
FIG. 4 is a showing of the third Moire pattern used in determining the index of refraction.

When using low grade optics the Moire patterns or fringes are somewhat distorted and determining $\alpha$ by making an actual measurement of the rotation on the original Moire fringe is cumbersome and prone to error. However, since the Moire pattern is also a grating, if it is double exposed another Moire pattern is obtained for the rotated Moire pattern superimposed on the nonrotated Moire pattern of the original gratings. The new Moire pattern has a pitch of p' as shown in FIG. 4. The fringes of the lines of the new Moire pattern are more straight than those of the original moire pattern because the double exposure cancels distortions.

The angle $\alpha$ is readily calculated from the following equation:

$$\alpha = 2 \sin^{-1}(p/2p').$$

The angle $\theta = 2 \sin^{-1}(po/2p)$.

Using the above equations it can be shown that the index of refraction of the sample fluid $$n_s = n_r + \frac{r_1 \theta \tan \alpha}{2\Delta} \text{ or } 1.3330 + \frac{r_1 \theta \tan(2 \sin^{-1} p/2p')}{2\Delta}$$

where the reference fluid is water and $n_r = 1.3330$.

The double exposure picture of FIG. 4 is as previously described another Moire pattern. Here the original Moire pattern pitch p is present in the gratings but the new pitch p' is obtained by the rotation of the gratings. Therefore utilizing the double exposure method it is only necessary to measure p and p' as well of course to know the index of refraction of the reference fluid to obtain the index of refraction of the new fluid.

In operation then the technician would first fill cell 13 with the reference fluid, turn on the collimator light source. The collimated light source used for the measurements is a 5 milliwatt HeNe laser and a 3 inch reflective telescope. The first Moire pattern is obtained on screen S and recorded. The reference fluid of the inner compartment of cell 13 is replaced by a sample fluid and the collimated light source is transmitted through the cell to the screen to double expose the film so that the rotated Moire pattern is superimposed on the original pattern to obtain a final Moire pattern. The pitches p and p' are found from the double exposed film. The index of refraction is computed from the pitches.

In place of the camera such items as video equipment, or a "go-no-go" light detector and iris arrangement can be used to determine if the deflection is a set amount.

It should be noted that not only the index of refraction of the sample fluid can be obtained but simultaneously therewith the index of refraction of vapor or gas above the sample fluid can also be obtained.

While the principles of the invention have been described above in connection with specific apparatus and application it is to be understood that this description is made by way of example only and not as a limitation on the scope of the invention.

We claim:

1. A system for determining the index of refraction of a sample fluid, said system comprising:
    collimated light source means,
    light pervious cell means for holding fluids and deflecting the light passing therethrough,
    grating means for establishing first Moire patterns using light from said collimated light source means transmitted through said cell means with a reference fluid therein, and second Moire patterns by replacing said reference fluid with said sample fluid, and
    means for superimposing said first Moire patterns on said second Moire patterns to thereby establish third Moire patterns, and
    means for measuring characteristics of the different Moire patterns to obtain the index of refraction of the sample fluid.

2. The system of claim 1 wherein said first and second patterns have a pitch p and said third pattern has a pitch p', and
    means for measuring p and p' to use in computing the index of refraction of said sample fluid.

3. The system of claim 1 wherein said cell means comprises an inner compartment defined by lenses.

4. The system of claim 3, wherein a pair of lenses are used, one on each side of said inner compartment.

5. The system of claim 4, wherein said pair of lenses are zero diopter lenses.

6. The system of claim 1, wherein said superimposing means comprises camera means for providing double exposures of the first and second Moire patterns to thereby provide the third Moire patterns.

7. The system of claim 1 wherein the pitch of the second Moire pattern is rotated relative to the pitch of the first Moire pattern.

8. The system of claim 2, wherein said cell means comprises an inner compartment defined by lenses.

9. The system of claim 8, wherein a pair of lenses are used, one on each side of said inner compartment.

* * * * *

UNITED STATES PATENT AND TRADEMARK OFFICE
CERTIFICATE OF CORRECTION

PATENT NO.   : 4,569,590
DATED        : February 11, 1986
INVENTOR(S)  : KARNY et al It is certified that error appears in the above—identified patent and that said Letters Patent is hereby corrected as shown below:

Column 4, line 15: change the term "$n_2$" at the end of the equation to read --$r_2$--.

Signed and Sealed this

Twenty-fourth Day of November, 1987

Attest:

DONALD J. QUIGG

*Attesting Officer*　　　*Commissioner of Patents and Trademarks*